(12) United States Patent
Varilla et al.

(10) Patent No.: US 11,957,378 B1
(45) Date of Patent: Apr. 16, 2024

(54) ANTI-MICROBIAL SURGICAL ACCESS DEVICE

(71) Applicant: Northgate Technologies, Inc., Elgin, IL (US)

(72) Inventors: Cornelio M. Varilla, Des Plaines, IL (US); Jacob M. Bumpus, Woodstock, IL (US); Ju-Hyoung Kim, Naperville, IL (US)

(73) Assignee: NORTHGATE TECHNOLOGIES, INC., Elgin, IL (US)

(*) Notice: Subject to any disclaimer, the term of this patent is extended or adjusted under 35 U.S.C. 154(b) by 0 days.

(21) Appl. No.: 17/555,856

(22) Filed: Dec. 20, 2021

Related U.S. Application Data

(60) Provisional application No. 63/127,507, filed on Dec. 18, 2020.

(51) Int. Cl.
| | | |
|---|---|---|
| *A61B 17/34* | (2006.01) | |
| *A61B 1/06* | (2006.01) | |
| *A61B 5/00* | (2006.01) | |
| *A61B 90/70* | (2016.01) | |

(52) U.S. Cl.
CPC ........ *A61B 17/3421* (2013.01); *A61B 1/0684* (2013.01); *A61B 5/0086* (2013.01); *A61B 90/70* (2016.02)

(58) Field of Classification Search
CPC ............... A61B 1/32; A61B 17/3421–3423
See application file for complete search history.

(56) References Cited

U.S. PATENT DOCUMENTS

| | | |
|---|---|---|
| 2,355,258 A | 5/1941 | Biggs et al. |
| 5,144,146 A | 9/1992 | Wekhof |
| 7,338,473 B2 | 3/2008 | Campbell et al. |
| 7,798,998 B2 | 9/2010 | Thompson et al. |
| 7,806,870 B2 | 10/2010 | Mastri et al. |
| 7,854,724 B2 | 12/2010 | Stearns et al. |
| 7,931,859 B2 | 4/2011 | Mlodzinski et al. |
| 8,715,219 B2 | 5/2014 | Stearns et al. |
| 8,795,223 B2 | 8/2014 | Steanrs et al. |

(Continued)

FOREIGN PATENT DOCUMENTS

| | | | |
|---|---|---|---|
| CN | 108652717 A | * | 10/2018 |
| CN | 110384550 A | * | 10/2019 |
| WO | WO 2012/005819 A1 | | 1/2012 |

OTHER PUBLICATIONS

U.S. Appl. No. 17/665,232, filed Feb. 4, 2022.

(Continued)

*Primary Examiner* — Eduardo C Robert
*Assistant Examiner* — Michelle C Eckman
(74) *Attorney, Agent, or Firm* — Crowell & Moring LLP

(57) ABSTRACT

A surgical access device, such as a trocar, for use in providing access to a patient in a surgical setting is disclosed. The surgical access device includes an irradiation component to inactivate and sterilize gas that accidentally escapes a pneumoperitoneum, or ambient gas from outside the patient that may become entrained into the pneumoperitoneum. The surgical access device may include a central lumen that is gasketless or implements a gasket. The irradiation source may include an ultraviolet radiation source on or in the body of the surgical access device, and may be part of a discrete, removable attachment to a main part of the surgical access device body.

23 Claims, 5 Drawing Sheets

(56) References Cited

U.S. PATENT DOCUMENTS

| | | | |
|---|---|---|---|
| 8,961,451 B2 | 2/2015 | Stearns et al. | |
| 9,017,281 B2 | 4/2015 | Mastri et al. | |
| 9,093,258 B2 | 7/2015 | Stibich et al. | |
| 9,806,229 B2 | 10/2017 | Kashima et al. | |
| 10,639,071 B2 | 5/2020 | Stearns et al. | |
| 2008/0279733 A1 | 11/2008 | Glazman | |
| 2012/0085927 A1 | 4/2012 | Maeng et al. | |
| 2012/0313532 A1* | 12/2012 | Stibich | A61L 2/10 362/277 |
| 2018/0228510 A1* | 8/2018 | Holsten | B01D 46/0097 |
| 2019/0167304 A1 | 6/2019 | Stearns et al. | |
| 2019/0254771 A1* | 8/2019 | Swift | A61B 1/00032 |
| 2021/0401451 A1* | 12/2021 | Fujii | A61B 17/00008 |
| 2022/0168013 A1* | 6/2022 | Baril | A61B 17/3423 |

OTHER PUBLICATIONS

David Welch, et al., "*Far-UVC light: A new tool to control the spread of airborne-mediated microbial diseases.*", Scientific Reports | (2018) 8:2752 | DOI:10.1038/s41598-018-21058-w; Feb. 9, 2018 (7 pages).

Ciara R. Huntington, et al., "Safety first: significant risk of air embolism in laparoscopic gasketless insufflation systems"; Surgical Endoscopy (2019) 33:3964-3969; Feb. 15, 2019 (6 pages).

R.P. Weenink, et al., "*The AirSeal® insufflation device can entrain room air during routine operation.*" Techniques in Coloproctology (2020) 24:1077-1082, Jul. 30, 2020, https://doi.org/10.1007/s10151-020-02291-w (6 pages).

\* cited by examiner

ANTI-MICROBIAL SURGICAL ACCESS DEVICE

CROSS-REFERENCE TO RELATED APPLICATIONS

This application claims the benefit of U.S. Provisional Patent Application No. 63/127,507, filed Dec. 18, 2020, the entirety of which is hereby incorporated herein by reference.

FIELD OF THE DISCLOSURE

The present disclosure relates to devices for use surgical settings and, more particularly, to an anti-microbial laparoscopic instrument.

BACKGROUND

In the field of laparoscopic surgery, the ability to create and maintain a surgical working space is often achieved through filling or "insufflating" the patient's peritoneal cavity with a gas such as carbon dioxide, creating what is called the "pneumoperitoneum". Access to this surgical working space is typically achieved through the use of a device such as a trocar, which serves as an opening through which surgical instruments may be inserted and which also serves to retain the gas inside the peritoneal cavity. Such trocars typically include a gasket or valve material which forms a unidirectional seal against the outward pressure of the pneumoperitoneum. However, such designs may still exhibit some loss of pneumoperitoneum pressure into the operating room through these gaskets, sometimes during instrument exchanges or if the instrument is used with a larger diameter trocar.

Other, less common trocar and pressure barrier designs and methods have been introduced, such as those in which a pressurized fluid is used to form a pressure barrier around the surgical instrument, to try and reduce the loss of pressure from the pneumoperitoneum. Such a method offers the benefit of reducing contact between the trocar and any surgical instruments therein. Such contact may inhibit the movement of such instruments, and, in the case of a laparoscope, transfer contaminants which inhibit clear visualization of the surgical space. However, present commercial embodiments of such gasketless trocar designs may also introduce unique problems, such as the entrainment of room air and the consequent risk of introduction of contaminants to the patient. This introduction of contaminants may infect the patient with microbes such as viruses and bacteria. Additionally, as with standard gasketed trocar designs, leakage out of the pneumoperitoneum is possible with gasketless trocars and may be even more pronounced, potentially exposing operating room staff to toxins from within the patient.

SUMMARY

According to a first aspect, a surgical access device for permitting access to a peritoneum is disclosed. The surgical access device includes a body having an instrument receiving region at a proximal end and a cannula at a distal end, where a diameter of the body is greater at the receiving region than at the cannula. The body defines a central lumen extending from the proximal end to the distal end. An irradiation circuit is mounted on the body, where the irradiation circuit positioned to direct sterilization energy into the central lumen to sterilize gas passing through the central lumen.

According to another aspect, a surgical access device is disclosed having an elongated tubular body that includes a proximal end and a distal end with a lumen extending along a longitudinal axis between the proximal and the distal ends. The proximal end of the elongated tubular body has an inner diameter greater than an inner diameter of the distal end. At least one irradiation element is positioned along the elongated tubular body and oriented to direct radiant energy toward the lumen. Additionally, the lumen extending through the elongated tubular body is gasket-free. In yet another aspect, a surgical access device for permitting access to a peritoneum includes a trocar body extending along a longitudinal axis, the trocar body defining a passageway extending therethrough having a proximal opening and a distal opening. The surgical access device also includes an instrument receiving region positioned at the proximal opening of the passageway and a cannula positioned at the distal opening of the passageway, where a diameter of the passageway is greater at the receiving region than at the cannula. A sterilization module is detachably connectable with the trocar body at the proximal opening. The sterilization module includes an annular-shaped extension body having an inner diameter substantially equal to an inner diameter of the proximal opening, as well as at least one irradiation element positioned on the extension body. The at least one irradiation element is configured to emit a sterilization energy to sterilize gas passing into or out of the passageway of the body.

DETAILED DESCRIPTION

In order to address the potential problems identified above, a surgical access device, such as a gasketless trocar, is disclosed that can reduce the chance of contamination from air entrainment from an operating theater into a pneumoperitoneum or the chance of contamination by air escaping from the pneumoperitoneum via the surgical access device.

Embodiments of a trocar system are disclosed herein that incorporate a sterilization component to sanitize any gas which is transported through its proximal center lumen. This mitigates the risk of patient infection during a room air entrainment event, as has been observed with gasketless access devices. It also mitigates the risk of infection to the operating room staff during leakage of unfiltered pneumoperitoneum gas through the proximal end of an access device, such as may occur with either a gasketed or gasketless access device. This sterilization component may utilize irradiation to inactivate any airborne microbes transported in said gas.

The sterilization component may utilize irradiation in the ultraviolet (UV) range, with a wavelength of 10-400 nm. In particular, the component may utilize irradiation in the UVC range, with a wavelength of 207-222 nm, and may have a transmission peak at 222 nm. Such a wavelength range has been demonstrated in literature as an effective antimicrobial which is still safe for exposed mammalian skin. The irradiation source may comprise an ultraviolet fluorescent lamp (an example of which is described in U.S. Pat. No. 2,355,258) or an ultraviolet light emitting diode (LED) (an example of which is described in U.S. Pat. No. 9,806,229). Further, the use of an optical filter mechanism may allow a customized transmission profile targeted to optimize antimicrobial efficacy and user safety. Thin-film filter technology has been well documented as being effective for wavelength transmission profile customization. Such an optical filter mechanism may be localized to the irradiation source (s), or may be incorporated into the overall construction of a portion or portion(s) of the proximal center lumen wall of the surgical access device.

As described in greater detail below, a laparoscopic instrument with one or more sterilization components is described. The laparoscopic instrument may be in the form of an access device to a peritoneum or other surgical site, such as a trocar, and/or may be a gasketless instrument in different implementations. The sterilization component(s), may include any of a number of irradiation modules configured to inactivate any airborne microbes transported in gas entering or exiting the gasketed or gasketless device. The irradiation module may be configured to emit light in the ultraviolet (UV) range, light in the far-UVC range, and/or may include the use of a thin-film filter with a bandpass range targeted to a desired wavelength for sterilizing entrained gas or escaping gas.

Figure 1:
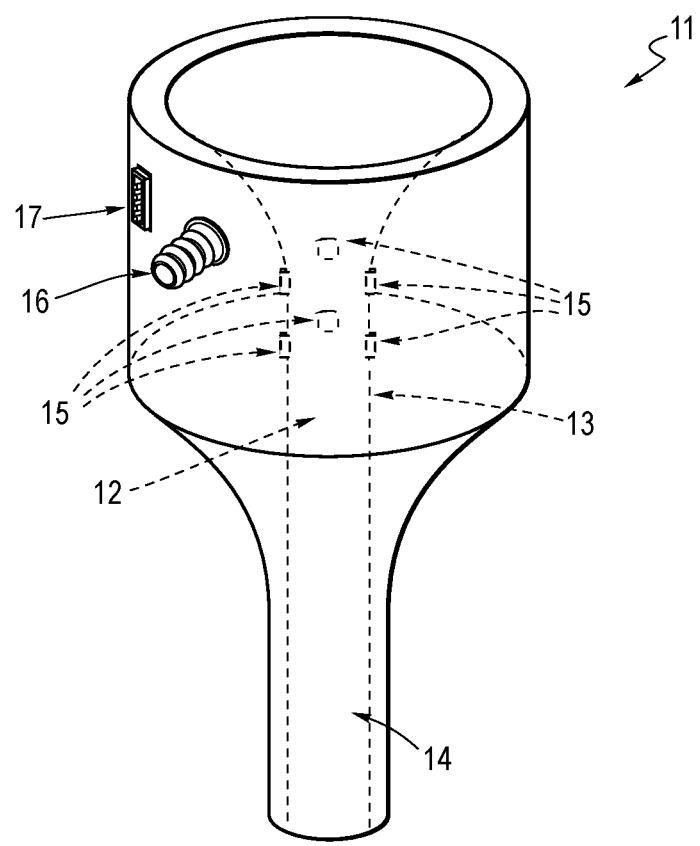
FIG. 1 is an isometric view of a gasketless access device according to one embodiment.
Figure 2:
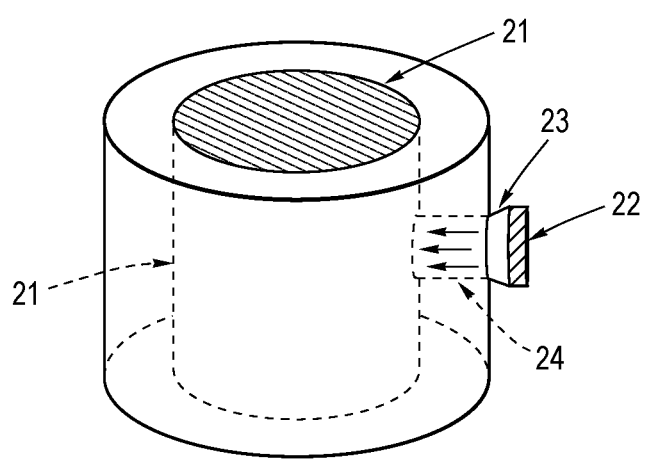
FIG. 2 is an isometric, cross-section, detail view of a proximal center lumen wall in the gasketless access device.
Figure 3:
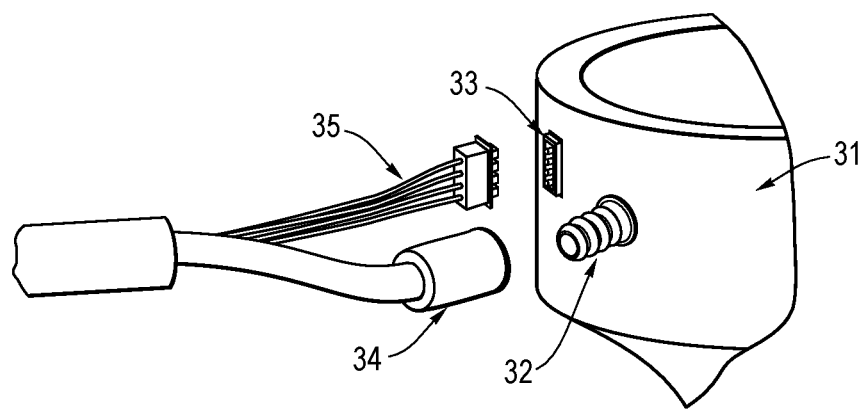
FIG. 3 is an isometric, detail view of fluid and electrical connectors on the gasketless access device of FIG. 1.

Referring to FIG. 1, a gasketless access device 11 is shown. The gasketless access device 11 includes a gasketless, proximal center lumen 12 extending through the proximal portion of the device 11 and confluent with the distal cannula 14. A proximal center lumen wall 13 may be made of opaque material. At least one irradiation module 15 is located at the perimeter of the proximal center lumen wall 13. The module 15 may be a light emitting diode (LED), preferably configured to emit an ultraviolet wavelength, such as in the far-UVC range. The modules 15 may instead consist of a fluorescent lamp or other radiation source. The module(s) 15 may be arranged on a flexible printed circuit board in one implementation. The gasketless access device 11 may also include a fluid connection port 16 and an electrical connection port 17 positioned on the exterior. In FIG. 2, a section of the device 11 having a version of the proximal center lumen wall 21 made of opaque material is illustrated, where an irradiation module 22 is located at the perimeter. An irradiation module filter 23 is located outside the center lumen wall and a wall perforation 24, oriented horizontally, allows collimated light to permeate the center lumen. FIG. 3 shows a sectional view of a gasketless access device 31 with an example of how the fluid connection port 32 and electrical connection port 33 may connect to a fluid conduit 34 having a connector compatible with the fluid connection port 32 and an electrical conduit 35 with connector compatible to the electrical connection port 33, respectively. The fluid conduit 34 may be, for example, insufflation tubing, and the electrical conduit 35 may be, for example, power lines for LED-type irradiation modules.

Figure 4:
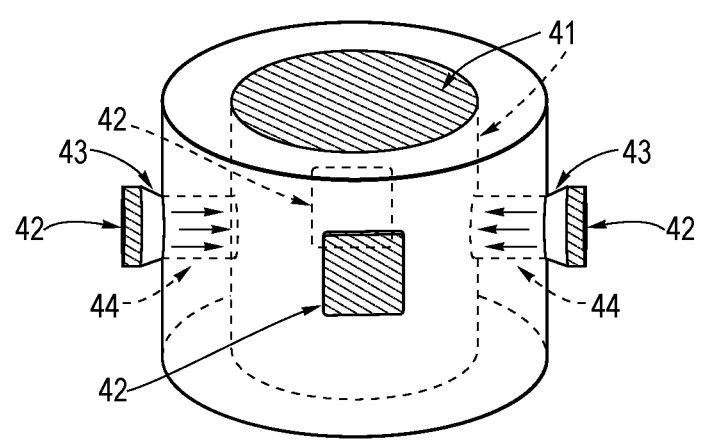
FIG. 4 is an isometric, detail view of an alternative embodiment of the proximal center lumen wall of FIG. 2.

Referring now to FIG. 4, a version of the proximal center lumen wall 41 of a gasketless access device is shown. In this implementation, the proximal center lumen wall 41 is opaque and multiple irradiation modules 42 are arranged circumferentially around the center lumen wall 41. Irradiation module filters 43 are associated with each irradiation module 42 and are located outside the center lumen wall 41 adjacent wall perforations 44 that allow collimated light to permeate the center lumen.

Figure 5:
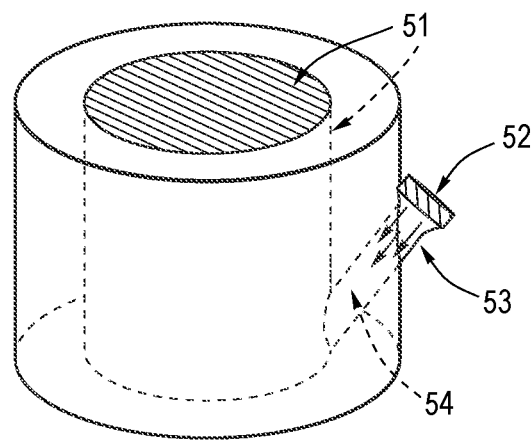
FIG. 5 is an isometric, detail view of a second alternative embodiment of the proximal center lumen wall of FIG. 2.

FIG. 5. illustrates an alternative version of the gasketless device of FIG. 2. In FIG. 5, the gasketless access device includes a proximal center lumen wall 51 made of opaque material and an irradiation module 52 is located at the perimeter and having an irradiation module filter 53 located outside the center lumen wall. However, the wall perforation 54 which allows collimated light to permeate the center lumen is oriented substantially vertically in this embodiment. Thus, more of the intensity of the energy emitted from the irradiation module is directed down the center lumen toward the cannula 14 and away from the operator of the gasketless access device due to the slanted angle of the wall perforation 54.

Figure 6:
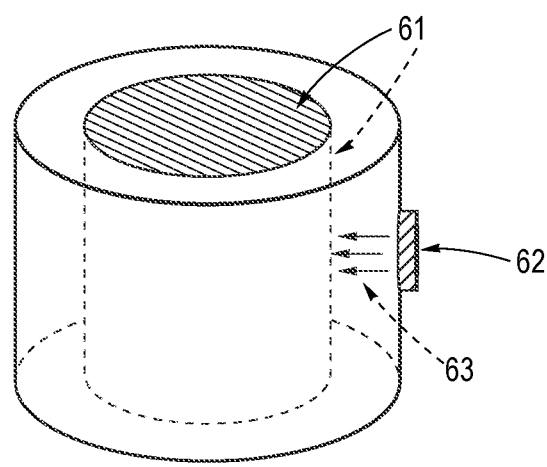
FIG. 6 is an isometric, detail view of a third alternative embodiment of the proximal center lumen wall of FIG. 2.

FIG. 6. illustrates an additional alternative version of the gasketless device of FIG. 2. In FIG. 6, the proximal center lumen wall 61 comprises an optical filter rather than simply an opaque surface. The irradiation module 62 does not require a separate irradiation module filter in this implementation. The optical filter of the proximal center lumen wall 61 may act to filter out light other than light in the bandpass frequency of the optical filter, allowing only light in the bandpass frequency to penetrate the optical filter and into the center lumen.

Figure 7:
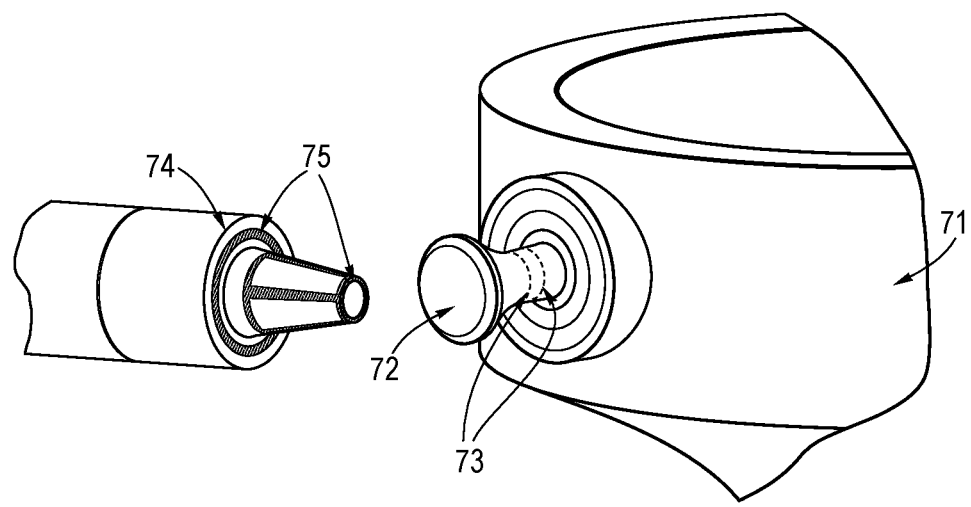
FIG. 7 is an isometric, detail view of an alternative embodiment of the fluid and electrical connectors of FIG. 3.

Referring to FIG. 7, an alternative fluid and electrical connection for the gasketless access device is shown. In the gasketless access device 71 of FIG. 7, a fluid connection port 72 and integrated electrical contacts 73 are shown as a unit on the exterior of the gasketless access device 71. In this embodiment, the closely spaced and/or integrated fluid and electrical ports 72, 73 permit the use of a combination fluid conduit 74 with integrated electrical conduit 75 each having respective connectors compatible with the fluid connection port 72 and integrated electrical contacts 73 on the gasketless access device 71.

Figure 8:
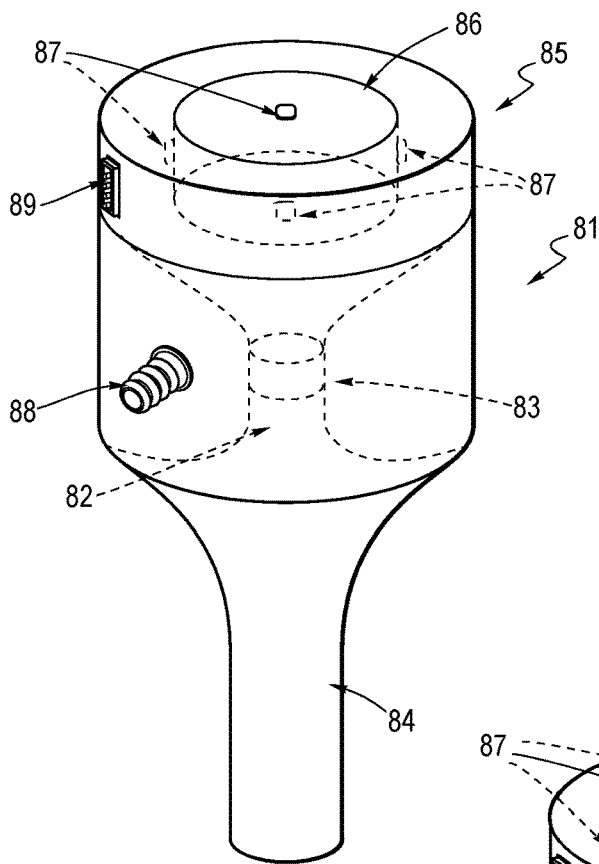
FIG. 8 is an isometric view of an embodiment of a gasketless access device having a detachable discrete proximal end attachment.
Figure 9:
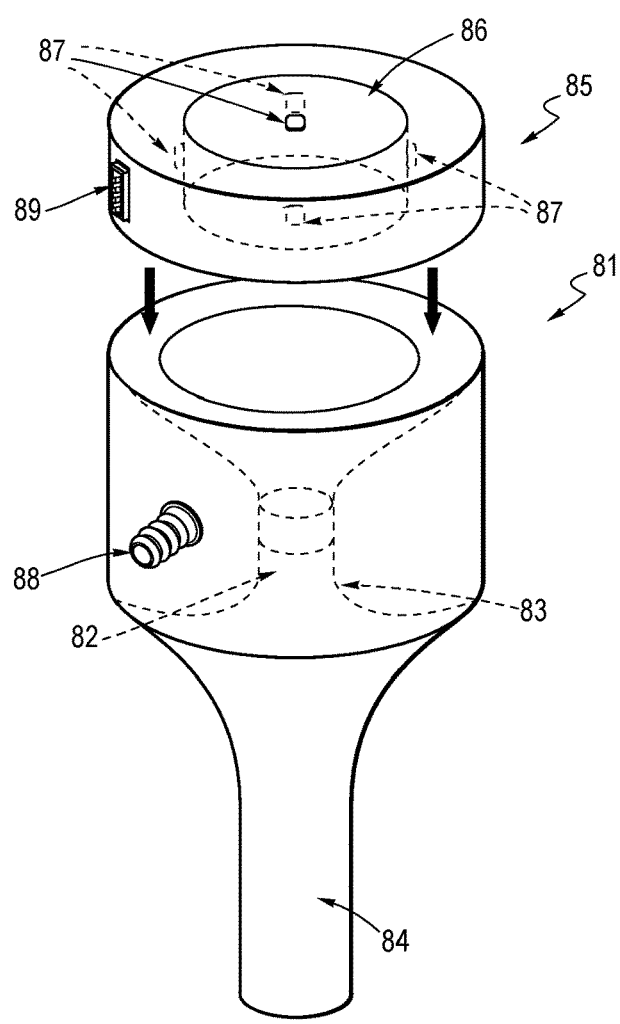
FIG. 9 is an isometric view of the gasketless device of FIG. 8 showing the discrete proximal end attachment in a detached state.

As best shown in FIGS. 8-9, in one embodiment a trocar or other gasketless access device 81 may include a discrete proximal end attachment 85 that is detachable. This embodiment of the gasketless access device 81 includes a gasketless, proximal center lumen 82 extending through the proximal portion of the device and confluent with the distal cannula 84. A proximal center lumen wall 83, made of opaque material, is positioned above the cannula 84. The discrete proximal end attachment 85 may be attached via mating threads, latches, clips, adhesive or other attachment mechanism. The discrete proximal end attachment 85 includes a discrete proximal end attachment center lumen 86 that aligns with, for example aligns coaxially with in one embodiment, the proximal center lumen 82 of the device 81. The irradiation module(s) 87 may be arranged circumferentially around the proximal end attachment 85. The irradiation module(s) 87 is preferably an LED light source. The LED of the irradiation module 87 may be tuned to emit an ultraviolet wavelength, preferably in the far-UVC range, and the irradiation module(s) 87 may be arranged on a flexible printed circuit board. A fluid connection port 88 may be included in the main body of the device 81 and an electrical connection port 89 may be located on the detachable discrete proximal end attachment.

In the embodiment of FIG. 8, the proximal end of the gasketless access device 81 receives a discrete proximal end attachment 85 which clips into place. The attachment comprises an electrical connection port 89, which is used to connect to an electrical conduit 35 as shown in FIG. 3. The electrical conduit 35 is used to conduct electricity to the proximal end attachment 85, which drives a plurality of irradiation modules 87. The irradiation modules 87 are positioned circumferentially around the inner diameter of the proximal end attachment, facing inward toward the center lumen 86, which is confluent with that of the access device 82. Each irradiation module may consist of an ultraviolet LED and thin-film filter with a peak transmission wavelength of 222 nm. In the event that gas enters through the proximal end of the access device 82, which may occur via entrainment as described in U.S. Pat. No. 10,639,071, any microbes borne on the gas will pass through the UV irradiation and thus be inactivated prior to entry into the distal cannula 84 and the patient. Likewise, in the event of pneumoperitoneum gas leakage out of the proximal end of the access device 82, which may occur during instrument exchanges or if the access device 81 is used with a smaller diameter instrument, any microbes borne on the gas will pass through the irradiation and thus be inactivated prior to entry into the operating room.

Although the specific drawings provided show a gasketless access device. any of the above embodiments described above, alone or in combination, may be implemented in a gasketed version of the access device in other implementations. The access device could have length similar to that of conventional laparoscopic trocars, between 40 and 200 mm. The fluid connection port and fluid conduit connector could have similar dimensions to that of typical ISO-594 Luer connections. The gasketless access device may use optical filters, more specifically thin-film filters. In certain implementations the filters may be bandpass filters designed to transmit the ultraviolet (UV) range, more specifically, in the UVC range (207-222 nanometers (nm)), more specifically, with a transmission peak at 222 nm.

Thin film filters used with the embodiments described above may include one or more of multiple different materials, including but not limited to: Silica, Alumina/sapphire, Hafnia, Zirconia, Magnesium Fluoride, Aluminum Fluoride, Lanthanum Fluoride, or Yttrium Fluoride. Suitable irradiation modules may include components such as SunTech LED Far UVC Led Light 207-220 nm-222 nm Far UV Led Chip, available from Shenzhen Suntech company located in Shenzhen, China. Flexible printed circuit board materials on which the irradiation modules may be located may include flexible plastic substrates, such as polyimide, PEEK or transparent conductive polyester, or screen-printed silver circuits on polyester.

The invention claimed is:

1. A surgical access device for permitting access to a peritoneum, the surgical access device comprising:
   a body having an instrument receiving region at a proximal end and
   a cannula at a distal end, wherein a diameter of the body is greater at the instrument receiving region than at the cannula;
   the body defining a central lumen extending from the proximal end to the distal end;
   an irradiation circuit mounted on the body, the irradiation circuit positioned to direct sterilization energy into the central lumen to sterilize gas passing through the central lumen; and
   wherein the irradiation circuit comprises an ultraviolet light source, the irradiation circuit is positioned on an end of an opening in a wall of the body, and the opening in the wall extends substantially perpendicularly through the wall and into the central lumen to permit collimated ultraviolet light to illuminate an interior portion of the central lumen.

2. The surgical access device of claim 1, further comprising a fluid port positioned on an exterior of the body closer to the proximal end than to the distal end, the fluid port configured to receive a fluid from a fluid source.

3. The surgical access device of claim 2, further comprising an electrical connector positioned on the exterior of the body closer to the proximal end than to the distal end, the electrical connector in electrical communication with the irradiation circuit and configured to receive electrical energy from an external power source.

4. The surgical access device of claim 2, wherein the proximal end of the body further comprises:
   a discrete proximal end attachment detachably connected to a remainder of the body;
   wherein the irradiation circuit is mounted to the discrete proximal end attachment; and
   wherein an electrical connector is positioned on an exterior of the discrete proximal end attachment and the electrical connector is in electrical communication with the irradiation circuit.

5. The surgical access device of claim 1, wherein the ultraviolet radiation source comprises a light emitting diode.

6. The surgical access device of claim 1, wherein the irradiation circuit further comprises a bandpass filter positioned on the ultraviolet radiation source, the bandpass filter constructed to only pass a limited range of an ultraviolet light spectrum emitted by the ultraviolet radiation source.

7. The surgical access device of claim 1, wherein the irradiation circuit further comprises a plurality of radiation sources positioned around the central lumen.

8. The surgical access device of claim 7, further comprising a plurality of radiation source filters, wherein each of the radiation source filters is positioned between a respective radiation source and the central lumen, and wherein each of the radiation source filters is configured to only pass a predetermined radiation frequency range emitted by the radiation sources.

9. The surgical access device of claim 8, wherein the plurality of radiation sources comprise ultraviolet light radiation sources, and the plurality of radiation source filters comprise thin-film bandpass filters constructed to only pass a limited range of an ultraviolet light spectrum emitted by the ultraviolet radiation sources.

10. A surgical access device comprising:
    an elongated tubular body having a proximal end and a distal end and having a lumen extending along a longitudinal axis between the proximal and the distal ends, wherein the proximal end of the elongated tubular body has an inner diameter greater than an inner diameter of the distal end;
    at least one irradiation element positioned along the elongated tubular body and oriented to direct radiant energy toward the lumen;

wherein the at least one irradiation element comprises an ultraviolet light source, the at least one irradiation element is positioned on an end of an opening in a wall of the elongated tubular body, and the opening in the wall extends substantially perpendicularly through the wall and into the lumen to permit collimated ultraviolet light to illuminate an interior portion of the lumen; and wherein the lumen extending through the elongated tubular body is gasket-free.

11. The surgical access device of claim 10, wherein an inner surface of the lumen is opaque.

12. The surgical access device of claim 10, wherein the elongated tubular body is transparent to ultraviolet light.

13. The surgical access device of claim 12, wherein a wall of the lumen in the elongated tubular body comprises a bandpass filter configured to only pass a predetermined portion of a bandwidth range of ultraviolent light.

14. The surgical access device of claim 13, further comprising an irradiation element filter positioned between the at least one irradiation element and the lumen, the irradiation element filter configured to permit only collimated light to pass into the lumen from the at least one irradiation element.

15. The surgical access device of claim 10, wherein the at least one irradiation element is positioned on a flexible circuit board.

16. The surgical access device of claim 10, wherein the ultraviolet light source comprises a light emitting diode.

17. The surgical access device of claim 10, wherein the irradiation circuit further comprises a bandpass filter positioned on the ultraviolet light source, the bandpass filter constructed to only pass a limited range of an ultraviolet light spectrum emitted by the ultraviolet light source.

18. The surgical access device of claim 10, wherein the irradiation circuit further comprises a plurality of radiation sources positioned around the central lumen.

19. The surgical access device of claim 18, further comprising a plurality of radiation source filters, wherein each of the radiation source filters is positioned between a respective radiation source and the central lumen, and wherein each of the radiation source filters is configured to only pass a predetermined radiation frequency range emitted by the radiation sources.

20. The surgical access device of claim 19, wherein the plurality of radiation sources comprises ultraviolet light radiation sources, and the plurality of radiation source filters comprise thin-film bandpass filters constructed to only pass a limited range of an ultraviolet light spectrum emitted by the ultraviolet radiation sources.

21. A surgical access device comprising:
an elongated tubular body having a proximal end and a distal end and having a lumen extending along a longitudinal axis between the proximal and the distal ends, wherein the proximal end of the elongated tubular body has an inner diameter greater than an inner diameter of the distal end;
at least one irradiation element positioned along the elongated tubular body and oriented to direct radiant energy toward the lumen, the irradiation element positioned outside the elongated tubular body; and
wherein the at least one irradiation element is positioned at an end of an opening in a wall of the elongated tubular body, wherein the opening in the wall extends through the wall at a non-perpendicular angle to the lumen to permit ultraviolet light to illuminate an interior portion of the lumen at an angle, such that the ultraviolet light is directed more toward the distal end of the lumen than the proximal end of the lumen.

22. The surgical access device of claim 21, further comprising a fluid port positioned on an exterior of the body closer to the proximal end than to the distal end, the fluid port configured to receive a fluid from a fluid source.

23. The surgical access device of claim 22, further comprising an electrical connector positioned on the exterior of the body closer to the proximal end than to the distal end, the electrical connector in electrical communication with the irradiation circuit and configured to receive electrical energy from an external power source.

\* \* \* \* \*